United States Patent [19]

Sato et al.

[11] Patent Number: 4,500,630
[45] Date of Patent: Feb. 19, 1985

[54] METHOD FOR FORMING MAGENTA COLOR IMAGE

[75] Inventors: Tadahisa Sato; Toshio Kawagishi; Nobuo Furutachi, all of Kanagawa, Japan

[73] Assignee: Fuji Photo Film Co., Ltd., Kanagawa, Japan

[21] Appl. No.: 580,303

[22] Filed: Feb. 15, 1984

[30] Foreign Application Priority Data

Feb. 15, 1983 [JP] Japan ................... 58-23434

[51] Int. Cl.³ .................... G03C 7/16; G03C 7/40
[52] U.S. Cl. .................... 430/386; 430/372; 430/387; 430/476; 430/551; 430/558
[58] Field of Search ............... 430/386, 387, 476, 551, 430/558, 372

[56] References Cited

U.S. PATENT DOCUMENTS

| | | | |
|---|---|---|---|
| 3,061,432 | 10/1962 | Menzel et al. | 430/558 |
| 3,199,983 | 8/1965 | Koepke et al. | 430/558 |
| 3,369,897 | 2/1968 | Menzel et al. | 430/558 |
| 3,649,278 | 3/1972 | Iwama et al. | 430/386 |
| 3,725,067 | 4/1973 | Bailey et al. | 430/476 |
| 4,338,393 | 7/1982 | Bailey et al. | 430/558 |

Primary Examiner—J. Travis Brown
Attorney, Agent, or Firm—Sughrue, Mion, Zinn, Macpeak and Seas

[57] ABSTRACT

A silver halide photosensitive material is developed with a developing solution containing an aromatic primary amine in the presence of a coupler represented by the following general formula (I):

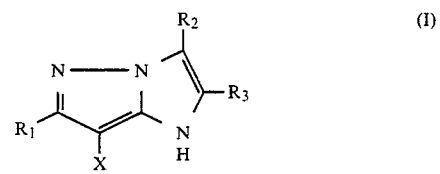

wherein $R_1$, $R_2$ and $R_3$ each represents a hydrogen atom or a certain substituent group, and X represents a hydrogen atom or a coupling eliminable group; to provide magenta color image having high color purity.

16 Claims, 2 Drawing Figures

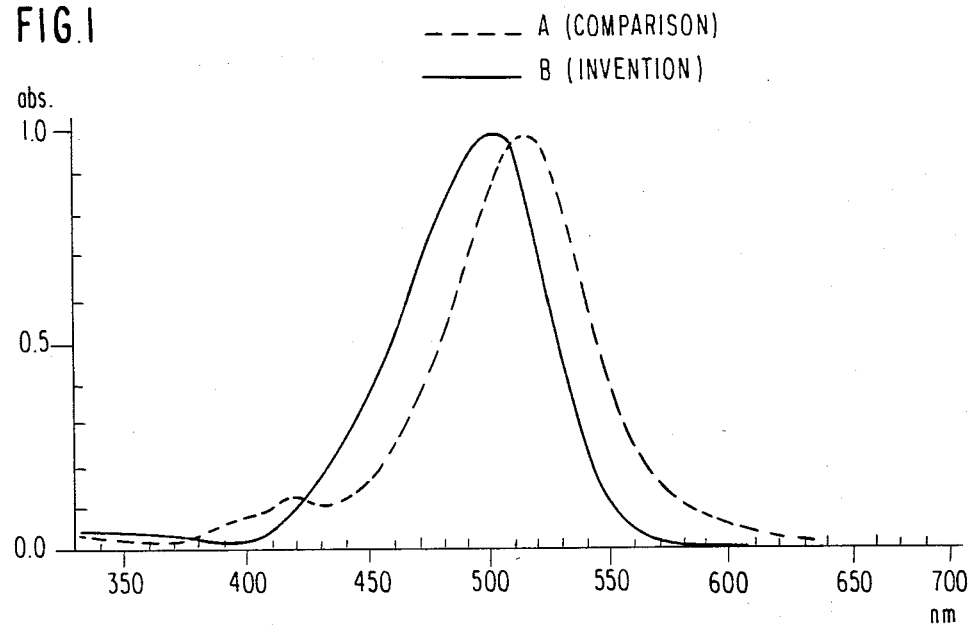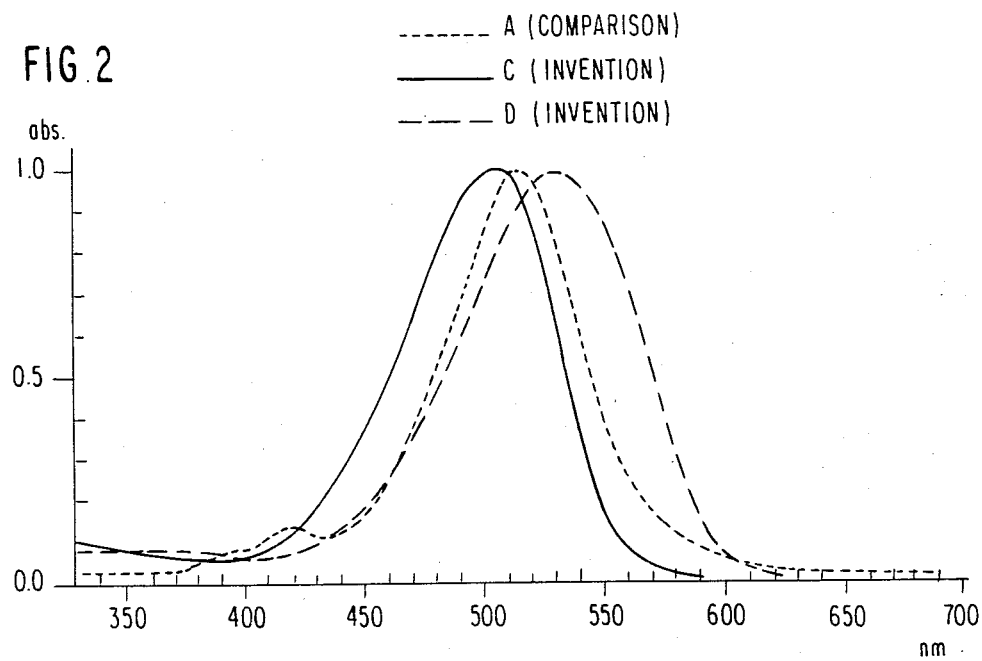

METHOD FOR FORMING MAGENTA COLOR IMAGE

FIELD OF THE INVENTION

The present invention relates to an image-forming method in which a novel magenta color image is formed. The image is formed through a coupling reaction with an aromatic primary amine being oxidized by optically exposed silver halide. More particularly, the invention relates to an image-forming method using an imidazo[1,2-b]pyrazole as a novel magenta coupler.

BACKGROUND OF THE INVENTION

It has been well known that the reaction of couplers with aromatic primary amine type color developing agents which are oxidized in advance using optically exposed silver halides as an oxidizing agent can afford indophenols, indoanilines, indamines, azomethines, phenoxazines, phenazines and dyes similar thereto and therethrough color images can be formed.

Now, let us concentrate our discussion on magenta color images. In order to form the magenta color image, couplers of 5-pyrazolone type, cyanoacetophenone type, indazolone type, pyrazolobenzimidazole type, and pyrazolotriazole type can be employed.

It is 5-pyrazolones that occupy most of magenta color image-forming couplers which have been prevailingly submitted to practical use heretofore, and of which wider and deeper studies have been made. Dyes formed from couplers of 5-pyrazolone type are excellent in fastness to heat and light, but they are known to have, in the vicinity of 430 nm, unnecessary absorption of light corresponding to the yellow component which causes turbidity to the resultant color.

For the purpose of reducing the above-described yellow component, a pyrazolobenzimidazole nucleus described in British Pat. No. 1,047,612; an indazolone nucleus described in U.S. Pat. No. 3,770,447; and a pyrazolotriazole nucleus described in U.S. Pat. No. 3,725,067 have been proposed as nuclear skeletons of couplers for forming magenta color images.

However, the magenta couplers described in the above-described patents leave something to be desired, since when mixed with silver halide emulsions in such a state that they are dispersed in hydrophilic protective colloids like gelatin, some of them provide unsatisfactory color images; some of them have low solubilities to high boiling point organic solvents; some of them are difficult of syntheses; and others can only exhibit comparatively low coupling activities when processed with usual developing solutions.

SUMMARY OF THE INVENTION

As a result of making a search for various new types of magenta color image forming couplers which do not exhibit the side absorption in the vicinity of 430 nm (because this side absorption is the most serious defect of 5-pyrazolone type couplers from the viewpoint of hue), the present inventors have found a series of couplers which have no side absorption in the shorter wavelength region, can provide color images of high fastness and can be relatively easily synthesized.

Therefore, a primary object of the present invention is to provide a new series of magenta color image-forming couplers which are excellent in not only color reproducibility but also color forming speed, maximum color formable density, ease of synthesis, and enable reduction of the amount of silver to be used by introducing an eliminable group at the coupling active position, that is, by converting them to the so-called 2-equivalent ones.

Another object of the present invention is to provide a magenta color image-forming method using this new series of couplers.

The above-described objects are attained by using as a coupler a novel imidazo[1,2-b]pyrazole type compound represented by the following general formula (I), and making this compound couple with an oxidation product of a developing agent to form a magenta color image:

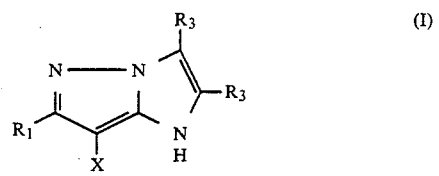

wherein $R_1$, $R_2$ and $R_3$ each represents a hydrogen atom or a certain substituent group, and X represents a hydrogen atom or a coupling eliminable group.

BRIEF DESCRIPTION OF THE DRAWINGS

FIG. 1 and FIG. 2 are absorption spectra of dyes produced from couplers in the manner described in Example 1, wherein A designates an absorption spectrum of the dye produced from Comparative Coupler A, B designates an absorption spectrum of the dye produced from Coupler (1) of the present invention, C designates an absorption spectrum of the dye produced from Coupler (8) of the present invention, and D designates an absorption spectrum of the dye produced from Coupler (9) of the present invention.

DETAILED DESCRIPTION OF THE INVENTION

In the foregoing general formula (I), substituents $R_1$, $R_2$ and $R_3$ each represents preferably a hydrogen atom, an aliphatic residue, an aryl group, a heterocyclyl group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclyloxy group, an acyloxy group, a carbamoyloxy group, a silyloxy group, an aryloxycarbonylamino group, an imido group, a heterocyclylthio group, a sulfinyl group, a phosphonyl group, an aryloxycarbonyl group, an acyl group, or an alkoxycarbonyl group; and the substituent X represents preferably a hydrogen atom, a halogen atom, a carboxy group, or a coupling eliminable group which is attached to the pyrazole nucleus through an oxygen atom, a nitrogen atom, a sulfur atom or a carbon atom. Further, $R_2$ and $R_3$ may combine with each other and form a 5-, 6- or 7-membered ring except aromatic rings. Furthermore, $R_1$ and $R_3$ each may be a halogen atom.

More specifically, the substituents $R_1$, $R_2$ and $R_3$ each represents a hydrogen atom; an aliphatic residue including straight and branched chain alkyl groups containing 1 to 32 carbon atoms, aralkyl groups, alkenyl groups, alkinyl groups, cycloalkyl groups and cycloalkenyl groups, which each may be substituted with a substituent which contains an oxygen atom, a nitrogen atom, a sulfur atom or a carbonyl group to be attached thereto, a hydroxy group, an amino group, a nitro group, a carboxyl group, a cyano group or a halogen atom, with the specific examples including a methyl group, a propyl group, a t-butyl group, a trifluoromethyl group, a tridecyl group, a 2-methanesulfonylethyl group, a 3-(3-pentadecylphenoxy)propyl group, a 3-{4-{2-[4-(4-hydroxyphenylsulfonyl)phenoxy]dodecanamido}phenyl}propyl}group, a 2-ethoxytridecyl group, a cyclopentyl group, a 3-(2,4-di-t-amylphenoxy)propyl group, etc.; an aryl group (e.g., a phenyl group, a 4-t-butylphenyl group, a 2,4-di-t-amylphenyl group, a 4-tetradecanamidophenyl group, etc.); a heterocyclyl group (e.g., a 2-furyl group, a 2-thienyl group, a 2-pyrimidinyl group, a 2-benzothiazolyl group, etc.); a cyano group; an alkoxy group (e.g., a methoxy group, an ethoxy group, a 2-methoxyethoxy group, a 2-dodecylethoxy group, etc.); an aryloxy group (e.g., a phenoxy group, a 2-methylphenoxy group, a 4-t-butylphenoxy group, etc.); an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.); an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.); a ureido group (e.g., a phenylureido group, a methylureido group, an N,N-dibutylureido group, etc.); a sulfamoylamino group (e.g., an N,N-dipropylsulfamoylamino group, an N-methyl-N-decylsulfamoylamino group, etc.); an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.); an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.); an alkoxycarbonylamino group (e.g., a methoxycarbonylamino group, a tetradecyloxycarbonylamino group, etc.); a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.); a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-t-amylphenoxy)propyl]carbamoyl group, etc.); a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.); a sulfonyl group (e.g., a methanesulfonyl group, an octanesulfonyl group, a benzenesulfonyl group, a toluenesulfonyl group, etc.); an alkoxycarbonyl group (e.g., a methoxycarbonyl group, a butyloxycarbonyl group, a dodecyloxycarbonyl group, an octadecyloxycarbonyl group, etc.); a heterocyclyloxy group (e.g., a 1-phenyltetrazol-5-oxy group, a 2-tetrahydropyranyloxy group, etc.); an acyloxy group (e.g., an acetoxy group, etc.); a carbamoyloxy group (e.g., an N-methylcarbamoyloxy group, an N-phenylcarbamoyloxy group, etc.); a silyloxy group (e.g., a trimethylsilyloxy group, a dibutylmethylsilyloxy group, etc.); an aryloxycarbonylamino group (e.g., a phenoxycarbonylamino group, etc.); an imido group (e.g., an N-succinimido group, an N-phthalimido group, a 3-octadecenylsuccinimido group, etc.); a heterocyclylthio group (e.g., a 2-benzothiazolylthio group, a 2,4-diphenoxy-1,3,5-triazole-6-thio group, a 2-pyridylthio group, etc.); a sulfinyl group (e.g., a dodecanesulfinyl group, a 3-pentadecylphenylsulfinyl group, a 3-phenoxypropylsulfinyl group, etc.); a phosphonyl group (e.g., a phenoxyphosphonyl group, an octyloxyphosphonyl group, a phenylphosphonyl group, etc.); an aryloxycarbonyl group (e.g., a phenoxycarbonyl group, etc.); and an acyl group (e.g., an acetyl group, a 3-phenylpropanoyl group, a benzoyl group, a 4-dodecyloxybenzoyl group, etc.). In the substituents $R_1$, $R_2$ and $R_3$, an alkyl group and an alkyl moiety contain 1 to 32 carbon atoms, and an aryl group and an aryl moiety contain 6 to 32 carbon atoms.

The substituent X represents a hydrogen atom; a halogen atom (e.g., a chlorine atom, a bromine atom, etc.); a carboxy group; a substituent group which has an oxygen atom at its bonding position (e.g., an acetoxy group, a propanoyloxy group, a benzoyloxy group, an ethoxyoxaloyloxy group, a pyruvyloxy group, a cinnamoyloxy group, a phenoxy group, a 4-cyanophenoxy group, a 4-methanesulfonamidophenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.); a substituent group which has a nitrogen atom at its bonding position (e.g., a benzenesulfonamido group, an N-ethyltoluenesulfonamido group, a pentafluorobutanamido group, a 2,3,4,5,6-pentafluorobenzamido group, an octanesulfonamido group, a p-cyanophenylureido group, an N,N-diethylsulfamoylamino group, a 1-piperidyl group, a 5,5-dimethyl-2,4-dioxo-3-oxazolidinyl group, a 1-benzyl-5-ethoxy-3-hydantoinyl group, a 2N-1,1-dioxo-3(2H)-oxo-1,2-benzoisothiazolidine group, a 2-oxo-1,2-dihydro-1-pyridyl group, an imidazolyl group, a pyrazolyl group, a 3,5-diethyl-1,2,3,4-tetrazol-1-yl group, a 5- or 6-bromobenzotriazol-1-yl group, a 5-methyl-1,2,3,4-triazol-1-yl group, a benzimidazolyl group, a 4-methoxyphenylazo group, a 4-pivaloylaminophenylazo group, a 2-hydroxy-4-propanoylphenylazo group, etc.); a substituent group which has a sulfur atom at its bonding position (e.g., a phenylthio group, a 2-carboxyphenylthio group, a 2-methoxy-5-t-octylphenylthio group, a 4-methanesulfonylphenylthio group, a 4-octanesulfonamidophenylthio group, a benzylthio group, a 2-cyanoethylthio group, a 5-phenyl-2,3,4,5-tetrazolylthio group, a 2-benzothiazolylthio group, a thiocyano group, an N,N-diethylthiocarbonylthio group, a dodecyloxythiocarbonylthio group, etc.); or a substituent group which has a carbon atom at its bonding position (e.g., a triphenylmethyl group, a hydroxymethyl group, a group of formula (II):

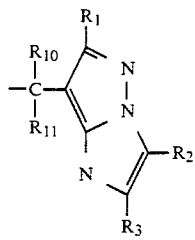

(II)

(wherein $R_{10}$ and $R_{11}$ each represents a hydrogen atom, an alkyl group, an aryl group, or a heterocyclyl group; and $R_1$, $R_2$ and $R_3$ each has the same meaning as defined hereinbefore), etc.). In the substituents $R_{10}$ and $R_{11}$, an alkyl group and an alkyl moiety contain 1 to 18 carbon atoms, and an aryl group and an aryl moiety contain 6 to 18 carbon atoms. Specific examples of the ring except aromatic rings which can be formed by connecting $R_2$ and $R_3$ to each other include a cyclopentene ring, a cyclohexene ring, and a cycloheptene ring.

Specific examples of the typical magenta couplers involved in the present invention are illustrated below. However, the magenta couplers which can answer the objects of the present invention should not be construed as being limited to the following examples.

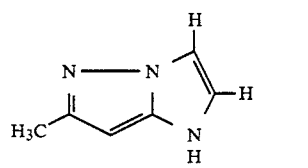

Coupler (1)

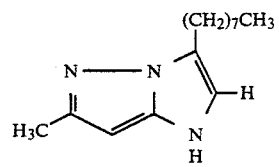

Coupler (2)

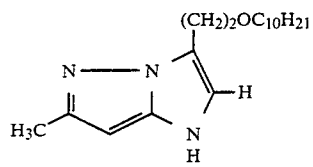

Coupler (3)

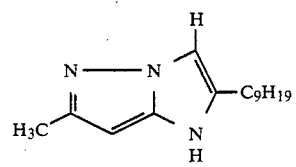

Coupler (4)

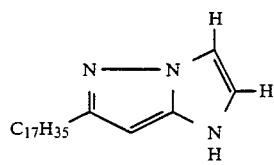

Coupler (5)

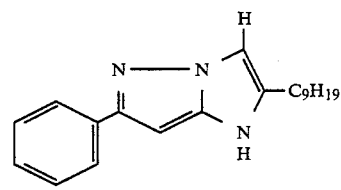

Coupler (6)

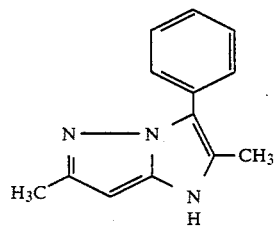

Coupler (7)

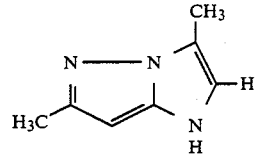

Coupler (8)

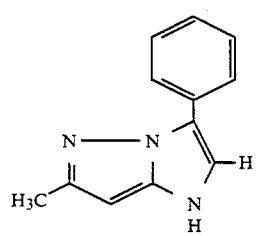

Coupler (9)

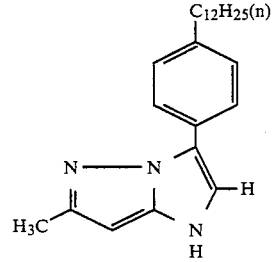

Coupler (10)

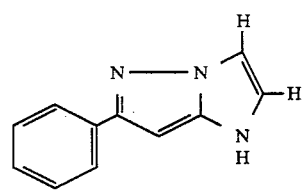

Coupler (11)

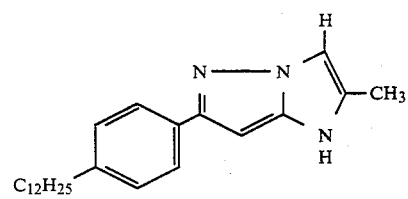

Coupler (12)

Coupler (13)
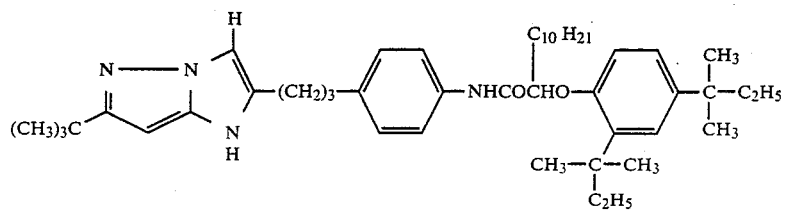
Coupler (14)
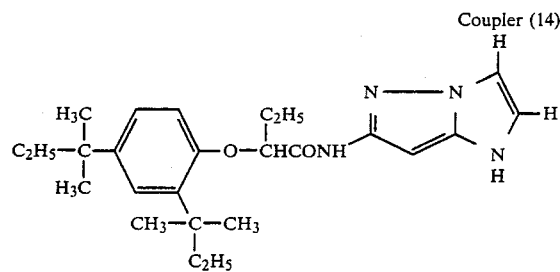
Coupler (15)
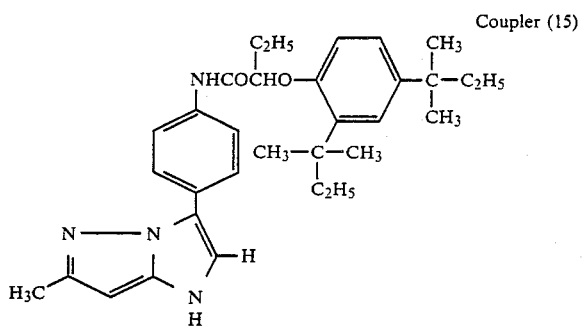
Coupler (16)
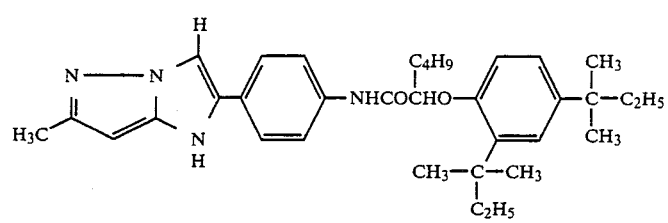
Coupler (17)
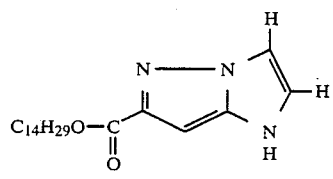
Coupler (18)
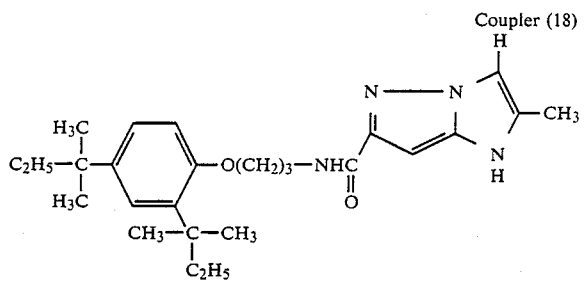
Coupler (19)
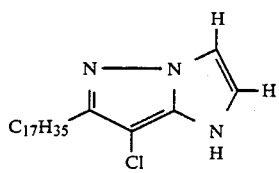
Coupler (20)
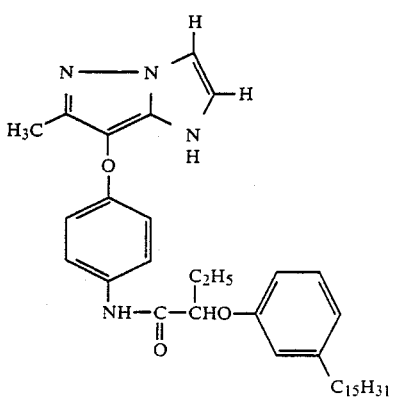

-continued
Coupler (21)
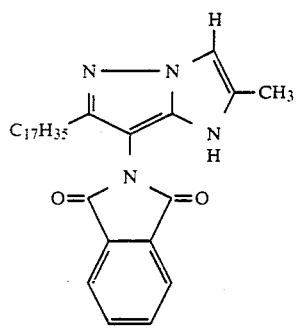
Coupler (22)
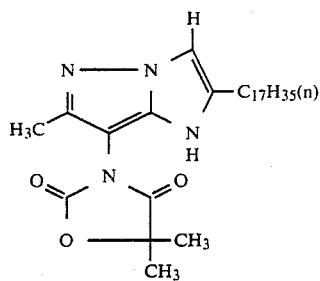
Coupler (23)
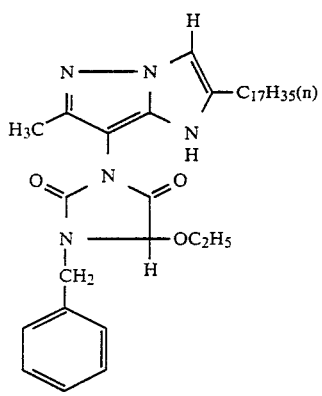
Coupler (24)
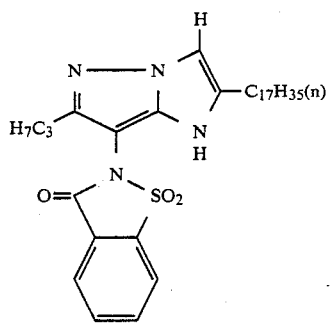
Coupler (25)
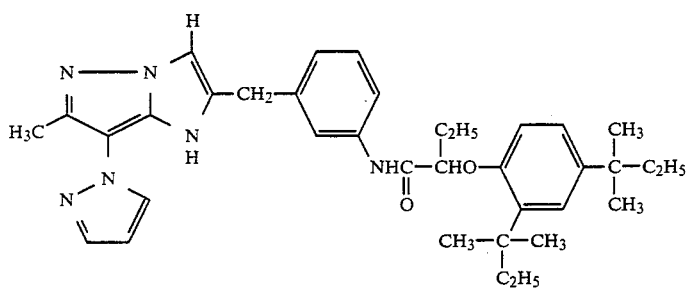
Coupler (26)
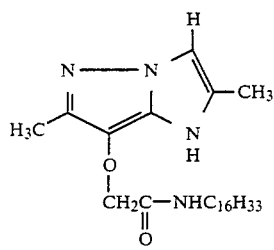
Coupler (27)
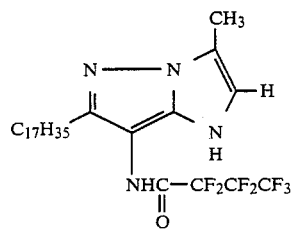
Coupler (28)
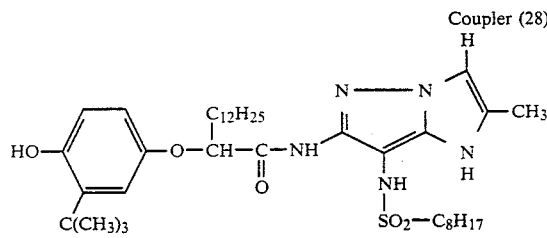
Coupler (29)
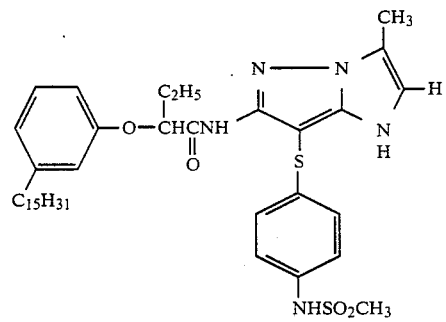

-continued
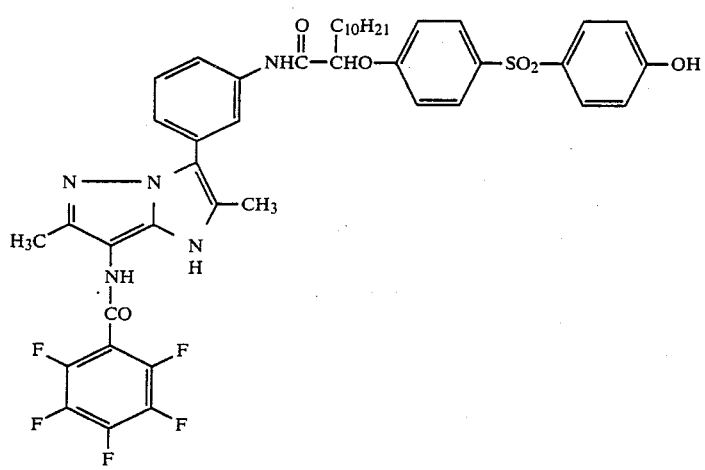
Coupler (30)
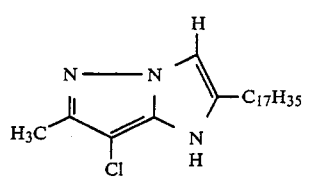
Coupler (31)
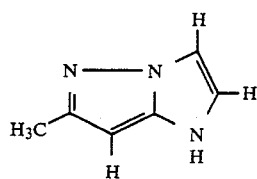
Coupler (32)
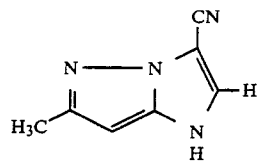
Coupler (33)
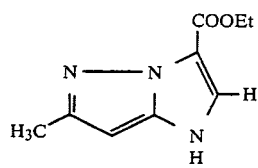
Coupler (34)
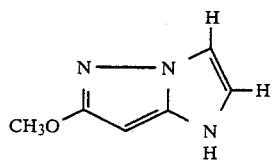
Coupler (35)
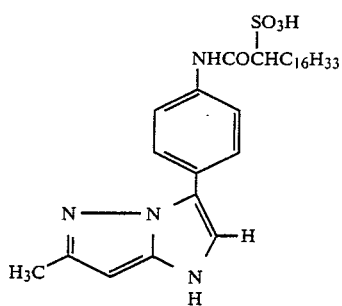
Coupler (36)
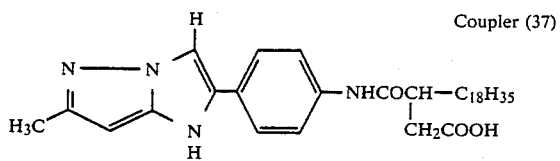
Coupler (37)
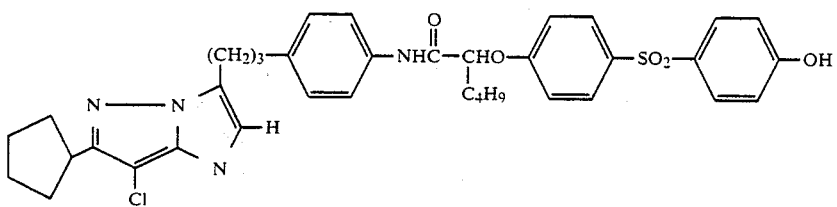
Coupler (38)

-continued
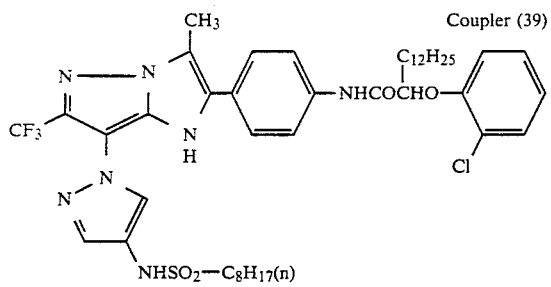
Coupler (39)
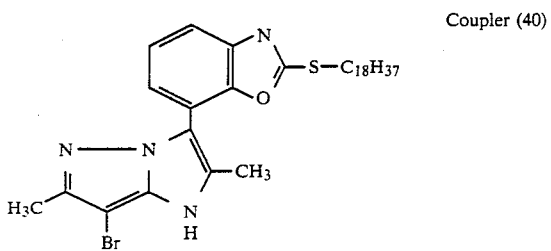
Coupler (40)
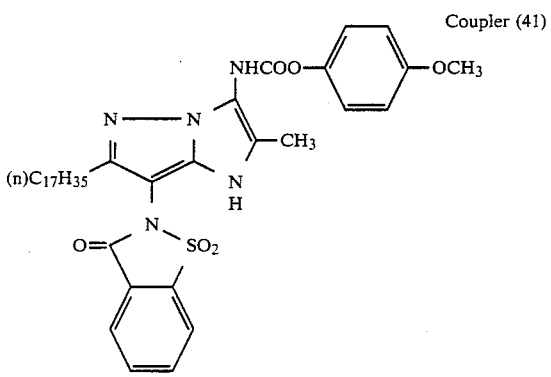
Coupler (41)
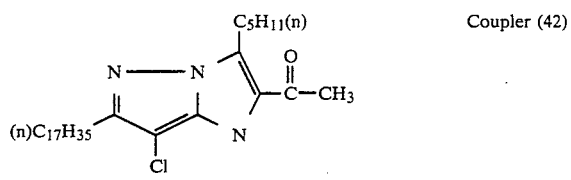
Coupler (42)
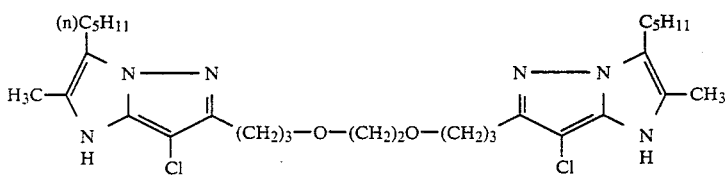
Coupler (43)
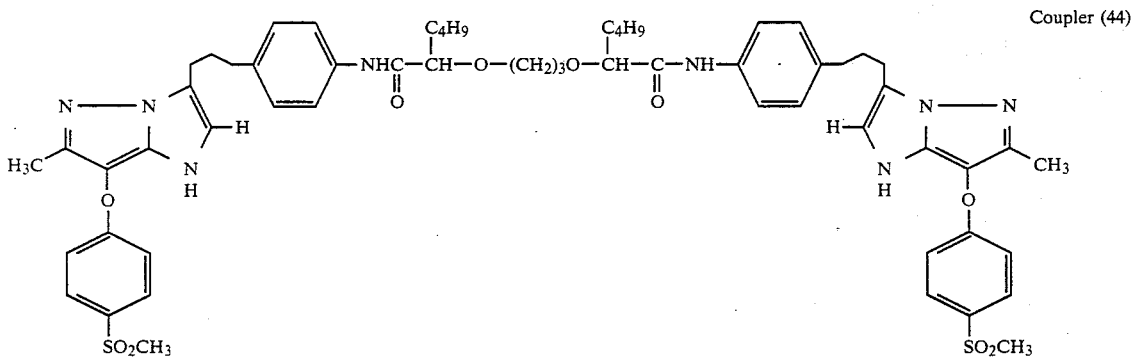
Coupler (44)

-continued

Coupler (45)

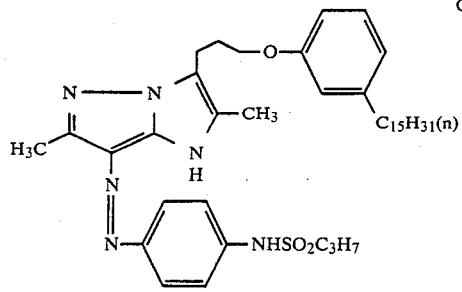

Coupler (46)

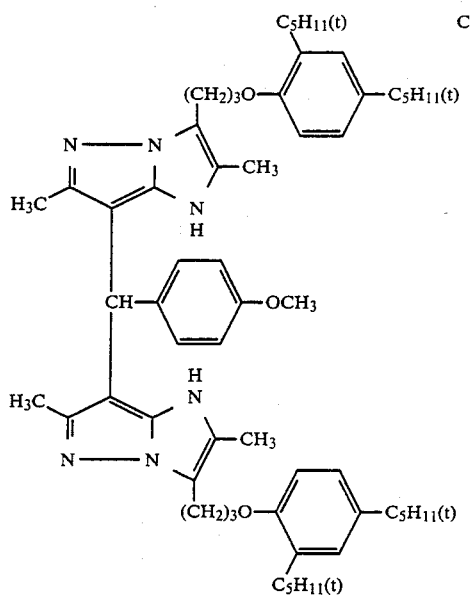

The couplers of the present invention can be synthesized using any one of the following four methods.

The first method is one which can be expressed by the following reaction scheme (1) described in J. Heterocyclic Chem., Volume 10, page 411 (1973).

Reaction Scheme (1)

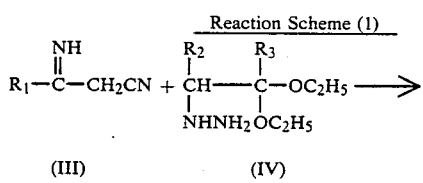

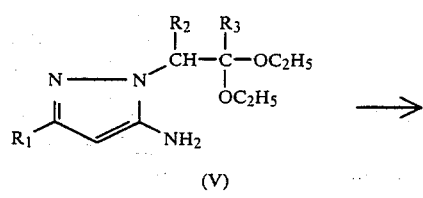

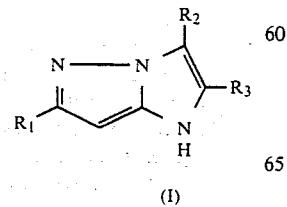

Compounds represented by the general formula (III) and compounds represented by the general formula (IV) can be synthesized by the methods described in the above-described literature, respectively. Therein, $R_1$ represents a hydrogen atom or an aryl group; $R_2$ represents a hydrogen atom, an alkyl group, an aryl group, an acyl group or a cyano group; and $R_3$ represents a hydrogen atom, an alkyl group, an aryl group or an alkoxy group.

The second method is one which can be expressed by the following reaction scheme (2).

Reaction Scheme (2)

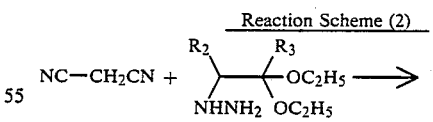

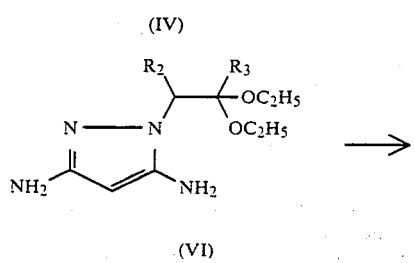

-continued
Reaction Scheme (2)

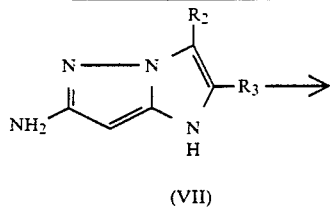

(VII)

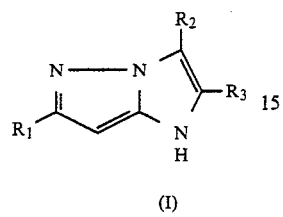

(I)

Various kinds of substituent groups can be introduced utilizing compounds of general formula (VII).

Therein, $R_1$ represents an acylamino group, a sulfonamido group, a ureido group, an alkoxycarbonylamino group, or a sulfamoylamino group; $R_2$ represents a hydrogen atom, an alkyl group, an aryl group, an acyl group or a cyano group; and $R_3$ represents a hydrogen atom, an alkyl group or an aryl group.

The third method is one which can be expressed by the following reaction scheme (3).

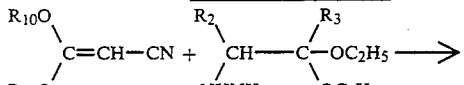

(VIII)          (IV)

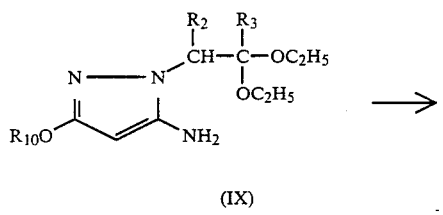

(IX)

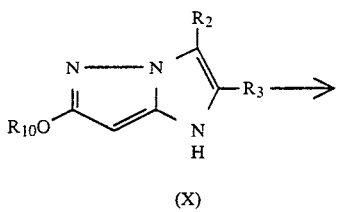

(X)

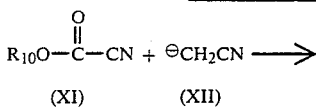

(I)

Therein, $R_{10}$ represents an alkyl group or an aryl group; $R_1$ represents an alkoxy group, an aryloxy group or an anilino group; $R_2$ represents a hydrogen atom, an alkyl group, an aryl group, an acyl group or a cyano group; and $R_3$ represents a hydrogen atom, an alkyl group or an aryl group.

The fourth method is one which can be expressed by the following reaction scheme (4).

Reaction Scheme (4)

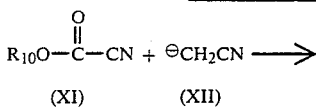

(XI)     (XII)

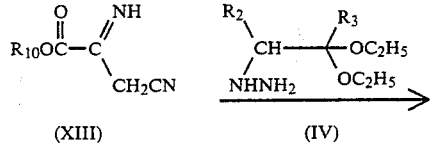

(XIII)          (IV)

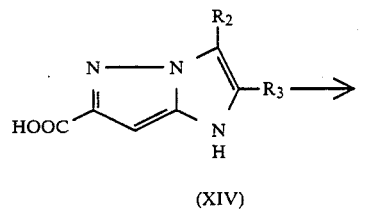

(XIV)

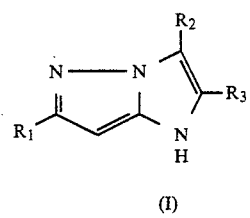

(I)

Therein, $R_1$ represents a carboxy group, a carbamoyl group, an acyl group, an amido group or an alkoxycarbonyl group; $R_2$ represents a hydrogen atom, an alkyl group, an aryl group, an acyl group or a cyano group; and $R_3$ represents a hydrogen atom, an alkyl group or an aryl group.

Other compounds involved in the scope of the claim of the present invention can also be synthesized by applying these methods.

General methods for introducing a coupling eliminable group to the coupler of the foregoing general formula (I) are illustrated below.

(a) Method for Connecting Oxygen Atom

The four equivalent couplers which constitute the mother nuclei of the couplers of the present invention, i.e., imidazo[1,2-b]pyrazole type couplers, are converted to dyes according to the method as described in Example 1. The resulting dyes are hydrolyzed in the presence of an acid catalyst to result in the conversion into their ketone bodies. These ketone bodies are reduced by hydrogenation in the presence of Pd-C catalyst, or with Zn-acetic acid, or with sodium borohydride to produce 7-hydroxy-imidazo[1,2-b]pyrazoles. The resulting pyrazoles are allowed to react with various kinds of halides. Thus, the intended couplers which have an oxygen atom as the connecting atom to the coupling eliminable group can be synthesized. (For details of the above-described method U.S. Pat. No. 3,926,631 and published unexamined Japanese Patent Application No. 70817/82 should be referred to.)

(b) Method for Connecting Nitrogen Atom

Methods for connecting a nitrogen atom can be broadly classified into three groups. Methods belonging to the first group comprise, as described in U.S. Pat. No. 3,419,391; introducing a nitroso group to the coupling active site using an appropriate nitrosating agent, reducing the nitroso group by a proper method (e.g., a hydrogenation method using Pd-C as a catalyst, a chemical reduction method using stannous chloride, etc., or so on) to convert to 7-amino-imidazo[1,2-b]pyrazole, and reacting the resultant aminated compound with some one of various kinds of halides. According to these methods, amide compounds can be principally synthesized.

Methods belonging to the second group comprise, as described in U.S. Pat. No. 3,725,067, halogenating the 7-position of an imidazo[1,2-b]pyrazolone with an appropriate halogenating agent, such as sulfuryl chloride, chlorine gas, bromine, N-chlorosuccinimide, N-bromosuccinimide, etc., and replacing the resultant halogen by a nitrogen-containing hetero ring in the presence of a proper base catalyst, such as triethylamine, sodium hydroxide, diazabicyclo[2,2,2]octane, anhydrous potassium carbonate, etc., according to the process described in published examined Japanese Patent Application No. 45135/81, resulting in the preparation of such a coupler that it is attached to the nitrogen atom at its 7-position. Similarly, compounds having a phenoxy group at the 7-position among compounds whose coupling eliminable groups are attached to the mother nuclei through their respective oxygen atoms can be synthesized using the above-described process.

Methods belonging to the third group are effective for the introduction of an aromatic nitrogen-containing hetero ring of $6\pi$- or $10\pi$-electron system to the 7-position, and specifically comprise, as described in published examined Japanese Patent Application No. 36577/82, adding two or more moles of aromatic nitrogen-containing hetero ring of $6\pi$- or $10\pi$-electron system to 1 mole of compound halogenated at its 7-position, which is prepared using the process described in the second group method, and heating the resultant mixture to 50° to 150° C. in the absence of any solvent, or to 30° to 150° C. in the presence of an aprotic polar solvent such as dimethylformamide, Sulfolane, hexamethylphosphotriamide or so on, resulting in the introduction of an aromatic nitrogen-containing heterocyclyl group to the 7-position in such a state that they are connected through the nitrogen atom.

(c) Method for Connecting Sulfur Atom

Couplers which have an aromatic or heterocyclic mercapto group as a substituent at their 7-position can be synthesized using the method described in U.S. Pat. No. 3,227,554. Specifically, an aryl mercaptan, a heterocyclyl mercaptan or the disulfide corresponding thereto is dissolved in a halogenated hydrocarbon type solvent, converted into sulfenyl chloride using chlorine or sulfuryl chloride and thereto, is added a 4-equivalent imidazo[1,2-b]pyrazole type coupler dissolved in an aprotic solvent, thus achieving the synthesis. For introducing an alkyl-mercapto group to the 7-position, the method described in U.S. Pat. No. 4,264,723; that is, one which comprises introducing mercapto group to the coupling active site of a coupler, and reacting the resultant mercapto group with a halide; and the method in which the synthesis is achieved in one step using S-(alkylthio)isothiourea and a hydrochloride (or a hydrobromide) are effective.

(d) Method for Connecting Carbon Atom

Couplers from which diarylmethane series compounds are eliminated can be synthesized by the method described in published examined Japanese Patent Application No. 34937/77, and aldehydebis type couplers can be synthesized using any one of the methods described in published unexamined Japanese Patent Application Nos. 105820/76, 129035/78 and 48540/79.

SYNTHESIS EXAMPLE 1

Synthesis of 6-methylimidazo[1,2-b]pyrazole (Coupler (1))

A mixture of 20 ml of anhydrous hydrazine and 31 g of bromoacetoaldehyde was heated in 100 ml of absolute ethanol under reflux for 6 hours. After cooling to room temperature, it was concentrated under reduced pressure. To the residue, ether and then, a concentrated aqueous solution of sodium hydroxide were added and stirred. Thereafter, the ether layer was separated, dried over potassium carbonate, and concentrated under reduced pressure. Thus, 14 g of crude hydrazinoacetoaldehyde diethyl acetal was obtained. It was distilled under reduced pressure to provide 10 g of pure substance (Yield 42%).

A mixture of 6.0 g portion of the resultant acetal and 3.3 g of diacetonitrile was heated in absolute ethanol under reflux for 15 hours. After removal of the solvent, the reaction mixture was distilled under reduced pressure. Thus, 6.0 g of 1-(2,2-diethoxyethyl)-5-amino-3-methylpyrazole (A) was obtained. Yield was 71%.

The resultant (A) was heated in a mixture of 200 ml of ethanol and 80 ml of a 20% aqueous solution of sulfuric acid under reflux for 5 hours. After cooling, excess solid sodium carbonate was added thereto. The resulting mixture was filtered, and the solvent was removed from the filtrate. The thus obtained residue was recrystallized to provide 1.4 g of 6-methylimidazo[1,2-b]pyrazole. Yield was 41%.

Melting Point: 177°–179° C.
Mass Spectrometry: 121 (M+, bp)
Elemental Analysis:

|  | C (%) | H (%) | N (%) |
| --- | --- | --- | --- |
| Calcd. | 59.49 | 5.82 | 34.69 |
| Found | 59.52 | 5.99 | 34.52 |

Nuclear Magnetic Resonance Spectrum (in CDCl$_3$): 2.39 (3H, S), 5.45 (1H, S), 6.76 (1H, d, J=2.3), 7.19 (1H, d, J=2.3)

SYNTHESIS EXAMPLE 2

Synthesis of 3,6-dimethylimidazo[1,2-b]pyrazolone (Coupler (8))

Hydrazinopropionaldehyde diethylacetal was prepared from α-bromopropionaldehyde diethylacetal obtained from propionaldehyde in a known manner. Therein, the yield was 50%.

From this acetal, 3,6-dimethylimidazo[1,2-b]pyrazole was prepared with a yield of 31% using the same process as described in Synthesis Example 1.

Melting Point: 202° C. (decomposed, in sealed tube)
Mass Spectrometry: 135 (M+, bp)
Elemental Analysis:

|  | C (%) | H (%) | N (%) |
|---|---|---|---|
| Calcd. | 62.20 | 6.71 | 31.09 |
| Found | 62.15 | 6.66 | 30.98 |

Nuclear Magnetic Resonance Spectrum (in DMSO-$d_6$): 2.37 (3H, d, J=1.8), 3.45 (3H, S), 5.47 (1H, S), 6.71 (1H, brq, J=1.8)

SYNTHESIS EXAMPLE 3

Synthesis of 6-methyl-3-phenylimidazo[1,2-b]pyrazole (Coupler (9))

Hydrazinophenylacetoaldehyde diethylacetal was prepared from phenylbromoacetoaldehyde diethylacetal obtained from phenylacetoaldehyde in a known manner. Therein, the yield was 66%. From this acetal, 6-methyl-3-phenylimidazo[1,2-b]pyrazole was prepared with a yield of 40% using the same process as described in Synthesis Example 1.

Melting Point: 190° C. (decomposed, in sealed tube)
Mass Spectrometry: 197 ($M^+$, bp)
Elemental Analysis:

|  | C (%) | H (%) | N (%) |
|---|---|---|---|
| Calcd. | 73.07 | 5.62 | 21.30 |
| Found | 73.15 | 5.58 | 21.21 |

Nuclear Magnetic Resonance Spectrum (in $CDCl_3$): 2.46 (3H, S), 5.54 (1H, S), 7.00 (1H, α, J=3.0), 7.28-7.50 (3H, m), 7.94-8.12 (2H, m)

SYNTHESIS EXAMPLE 4

Synthesis of Analogous Couplers (Coupler (2), Coupler (5) and Coupler (19))

All of these couplers can be synthesized in a similar manner to the above-described one.

The coupler of the present invention may be added to either a sensitive material or a color developing bath. In case of adding the coupler to a sensitive material, a suitable addition amount thereof ranges from $2 \times 10^{-3}$ mole to $5 \times 10^{-1}$ mole, particularly from $1 \times 10^{-2}$ mole to $5 \times 10^{-1}$ mole, per 1 mole of silver halide. On the other hand, when added to a color developing bath, it is used in an amount of 0.001 to 0.1 mole, preferably 0.01 to 0.05 mole, per 1,000 ml of the bath.

Examples of conventional couplers which can be employed in the present invention, in addition to the couplers of the present invention, include dye forming couplers as described below, that is, compounds capable of forming colors through the oxidative coupling with an aromatic primary amine developer (e.g., phenylenediamine derivatives, aminophenol derivatives, etc.) in the color development processing. More specifically, suitable examples of the conventional magenta coupler which can be used include 5-pyrazolone type couplers, pyrazolobenzimidazole type couplers, cyanoacetylcumarone type couplers, open-chain acylacetonitrile type couplers and so on. Suitable examples of the yellow coupler which can be used include acylacetamide type couplers (e.g., benzoylacetanilides, pivaloylacetanilides, etc.) and so on. Suitable examples of the cyan coupler which can be used include naphthol type couplers, phenol type couplers and so on. Among these couplers, those which are rendered non-diffusible by having a hydrophobic group called a ballast group, or polymerized ones are employed to greater advantage. These couplers may be either 4-equivalent or 2-equivalent to silver ion. In addition, colored couplers having a color correcting effect, or couplers capable of releasing a development inhibitor with the progress of development (the so-called DIR coupler) can be employed.

Further, colorless DIR coupling compounds which can give colorless products upon the coupling reaction and release development restrainers can be employed besides DIR couplers.

As for the above-described couplers and the like, two or more thereof can be incorporated together in the same layer for the purpose of satisfying characteristics required of the sensitive material, and one coupler may, of course, be added to two or more of layers.

In order to introduce a coupler as described above into a silver halide emulsion layer, known methods, e.g., one described in U.S. Pat. No. 2,322,027, etc., can be employed. Specifically, the coupler is dissolved in a high boiling point organic solvent, such as phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate, etc.), citric acid esters (e.g., tributyl acetylcitrate, etc.), benzoic acid esters (e.g., octylbenzoate, etc.), alkylamides (e.g., diethyllaurylamide, etc.), fatty acid esters (e.g., dibutoxyethyl succinate, diethyl azelate, etc.), trimesic acid esters (e.g., tributyl trimesate, etc.), etc., or in an organic solvent having a boiling point of about 30° C. to 150° C., such as lower alkyl acetates (e.g., ethyl acetate, butyl acetate, etc.), ethyl propionate, secondary butyl alcohol, methyl isobutyl ketone, β-ethoxyethyl acetate, methyl Cellosolve acetate, etc.; and then dispersed into a hydrophilic colloid. The above-described high boiling point organic solvents and low boiling point organic solvents may be used in a mixed form.

Also, the dispersing method utilizing specific polymers as described in published examined Japanese Patent Application No. 39853/76 and published unexamined Japanese Patent Application No. 59943/76 can be employed.

On the occasion that the coupler has an acid group such as carboxylic acid, sulfonic acid, etc., it is introduced into a hydrophilic colloid in the form of an alkaline aqueous solution.

It is convenient to choose photographic color couplers to be used so as to provide images of medium scale. It is desired that cyan dyes formed from cyan couplers exhibit maximum absorption bands in the wavelength range of about 600 nm to 720 nm, magenta dyes formed from magenta couplers exhibit their maximum absorption bands in the wavelength range of about 500 nm to 580 nm, and yellow dyes formed from yellow couplers exhibit their maximum absorption bands in the wavelength range of about 400 nm to 480 nm.

The sensitive materials prepared in accordance with embodiments of the present invention may contain as a color fog inhibitor hydroquinone derivatives, aminophenol derivatives, gallic acid derivatives, ascorbic acid derivatives and the like. Specific examples of color fog inhibitors which can be used include those described in U.S. Pat. Nos. 2,360,290, 2,336,327, 2,403,721, 2,418,613, 2,675,314, 2,701,197, 2,704,713, 2,728,659, 2,732,300 and 2,735,765, published unexamined Japanese Patent Application Nos. 92988/75, 92989/75, 93928/75, 110337/75 and 146235/77, published examined Japanese Patent Application No. 23813/75, and so on.

The sensitive materials prepared in accordance with embodiments of the present invention may contain ultraviolet absorbing agents in their hydrophilic colloidal layers. Suitable examples of such an ultraviolet absorbing agent include benzotriazole compounds substituted with an aryl group (e.g., those described in U.S. Pat. No. 3,533,794), 4-thiazolidone compounds (e.g., those described in U.S. Pat. Nos. 3,314,794 and 3,352,681), benzophenone compounds (e.g., those described in published unexamined Japanese Patent Application No. 2784/71), cinnamic acid ester compounds (e.g., those described in U.S. Pat. Nos. 3,705,805 and 3,707,375), butadiene compounds (e.g., those described in U.S. Pat. No. 4,045,229) and benzoxidol compounds (e.g., those described in U.S. Pat. No. 3,700,455). In addition, those described in U.S. Pat. No. 3,499,762 and those described in published unexamined Japanese Patent Application No. 48535/79 can also be employed. Further, couplers which have ultraviolet absorbing abilities (e.g., α-naphthol type cyan dye forming couplers) and polymers which have ultraviolet absorbing abilities may be employed. These ultraviolet absorbing agents may be fixed to a particular layer with a mordant.

The sensitive materials prepared in accordance with embodiments of the present invention may contain water-soluble dyes in their hydrophilic colloidal layers as a filter dye or for various purposes such as antiirradiation and so on. Suitable examples of such a dye include oxonol dyes, hemioxonol dyes, styryl dyes, merocyanine dyes, cyanine dyes and azo dyes. Among these dyes, oxonol dyes, hemioxonol dyes and merocyanine dyes are more useful. Specific examples of the dye which can be used are described in British Patent Nos. 584,609 and 1,177,429, published unexamined Japanese Patent Application Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312 and 4,070,352.

Photographic emulsions which can be used in the present invention may be spectrally sensitized with methine dyes or the others. Examples of such dyes include cyanine dyes, merocyanine dyes, complex cyanine dyes, complex merocyanine dyes, holopolar cyanine dyes, hemicyanine dyes, styryl dyes and hemioxonol dyes. Among these dyes, especially useful dyes are those belonging to cyanine dyes, merocyanine dyes, or complex merocyanine dyes. Any one of nuclei which are usually used in cyanine dyes as a basic heterocyclic nucleus is applicable to these dyes. Specifically, pyrroline nuclei, oxazoline nuclei, thiazoline nuclei, pyrrole nuclei, oxazole nuclei, thiazole nuclei, selenazole nuclei, imidazole nuclei, tetrazole nuclei, pyridine nuclei and the like; nuclei formed by any one of the above-described nuclei and any one of alicyclic hydrocarbon rings being fused together; and nuclei formed by any one of the above-described nuclei and any one of aromatic hydrocarbon rings being fused together, with specific examples including indolenine nuclei, benzindolenine nuclei, indole nuclei, benzoxazole nuclei, naphthoxazole nuclei, benzothiazole nuclei, naphthothiazole nuclei, benzoselenazole nuclei, benzimidazole nuclei, quinoline nuclei and so on are applicable. These nuclei may have some substituents on their carbon atoms.

To merocyanine dyes or complex merocyanine dyes, 5- or 6-membered heterocyclic nuclei such as pyrazoline-5-one nuclei, thiohydantoin nuclei, 2-thioxazolidine-2,4-dione nuclei, thiazolidine-2,4-dione nuclei, rhodanine nuclei, thiobarbituric acid nuclei and so on are applicable as a nucleus having a ketomethylene structure.

Specific examples of useful sensitizing dyes include those described in German Patent No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, and published examined Japanese Patent Application Nos. 14030/69 and 24844/77.

These sensitizing dyes may be employed individually or in combination. Combinations of sensitizing dyes are often employed for the purpose of supersensitization. Typical examples of supersensitizing combinations are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281 and 1,507,803, published examined Japanese Patent Applications Nos. 4936/68 and 12375/78, and published unexamined Japanese Patent Application Nos. 110618/77 and 109925/77.

Materials which can exhibit a supersensitizing effect in a combination with a certain sensitizing dye although they themselves do not spectrally sensitize silver halide emulsions or do not absorb light in the visible region may be incorporated into the silver halide emulsions. For example, aminostilbene compounds substituted with nitrogen-containing heterocyclic groups (for instance, as described in U.S. Pat. Nos. 2,933,390 and 3,635,721), aromatic organic acid-formaldehyde condensates (for instance, as described in U.S. Pat. No. 3,743,510), cadmium salts, azaindene compound and so on can be used. Particularly useful combinations are disclosed in U.S. Pat. Nos. 3,615,613, 3,615,641, 3,617,295 and 3,635,721.

Photographic processings for the sensitive materials of the present invention can be carried out using conventional methods. Therein, known processing solutions can be used. A processing temperature is generally selected from the range of 18° C. to 50° C. Of course, temperatures lower than 18° C. or higher than 50° C. may be employed. Either a development processing for forming silver image (black-and-white photographic processing) or a color photographic processing comprising of a development processing for forming color image may be applied depending upon the end-use purpose of the sensitive material.

A color developing solution is generally an alkaline aqueous solution containing a color developing agent. As a color developing agent, known primary aromatic amine developers, such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-β-methanesulfonamidoethylaniline, 4-amino-3-methyl-N-ethyl-N-β-methoxyethylaniline, etc.) can be used.

In addition to the above-described developers, those described in L. F. A. Mason, *Photographic Processing Chemistry*, pages 226–229, Focal Press, London (1966), U.S. Pat. Nos. 2,193,015 and 2,592,364, published unexamined Japanese Patent Application No. 64933/73, and so on can be used.

A color developing solution can additionally contain a pH buffering agent, such as sulfites, carbonates, borates and phosphates of alkali metals; a development restrainer or an antifoggant, such as bromides, iodides and organic antifoggants; and, if desired, a water softener, a preservative like hydroxyamine, an organic solvent such as benzyl alcohol or diethylene glycol, a development accelerator such as polyethylene glycol, quaternary ammonium salts or amines, dye forming couplers, competing couplers, a fogging agent like sodium borohydride, an auxiliary developer like 1-phenyl-3-pyrazolidone, a viscosity imparting agent, a chelating agent of polycarboxylic acid type described in U.S. Pat. No. 4,083,723; an antioxidant described in German Patent Application (OLS) 2,622,950; and so on.

After color development, the photographic emulsion layers are generally subjected to a bleach processing. A bleach processing and a fixation processing may be carried out either simultaneously or sequentially. Suitable examples of the bleaching agent which can be used include compounds of polyvalent metals such as Fe(III), Co(III), Cr(VI), Cu(II), etc., peroxy acids, quinones, nitroso compounds and so on. More specifically, ferricyanide compounds; dichromates; organic complex salts of Fe(III) or Co(III), such as complex salts of organic acids (e.g., aminopolycarboxylic acids such as ethylenediaminetetraacetic acid, nitrilo-triacetic acid, 1,3-diamino-2-propanoltetraacetic acid, etc., citric acid, tartaric acid, malic acid, and so on); persulfates; permanganates; nitrosophenols; and so on can be used. Among the above-described compounds, potassium ferricyanide, sodium ethylenediaminetetraacetoferrate(III), and ammonium ethylenediaminetetraacetateferrate(III) are especially useful. Ethylenediaminetetraacetatoiron(III) complex salts are useful in both an independent bleaching solution and a combined bleaching and fixing bath.

To a bleaching solution or a blix solution, a bleaching accelerator as described in U.S. Pat. Nos. 3,042,520 and 3,241,966, published examined Japanese Patent Application Nos. 8506/70 and 8836/70, and so on, a thiol compound as described in published unexamined Japanese Patent Application No. 65732/78, and various additives can be optionally added.

Silver halide emulsions to be used in the present invention are prepared generally by mixing a solution of a water-soluble silver salt (e.g., silver nitrate) with a solution of a water-soluble halogenide (e.g., potassium bromide) in the presence of a solution of a water-soluble high polymer (e.g., gelatin). Silver halides which may be produced include not only silver chloride and silver bromide, but also mixed silver halides such as silver chlorobromide, silver iodobromide, silver chloroiodobromide and so on. A mean grain size of silver halide grains produced (the grain size refers to the grain diameter when grains are spherical or nearly spherical, whereas when grains have a cubic form, it is determined by a projected area method taking a length of edge as a grain size) is preferably 2 μm or less, especially 0.4 μm or less. The distribution of the grain size can be either narrow or broad.

These silver halide grains may have the crystal form of cube, an octahedron, a composite form thereof, or so on.

Also, two or more silver halide photographic emulsions which are produced separately may be used in a mixture. Further, the interior and the surface of the silver halide grains may differ, or the silver halide grains may be uniform throughout. Furthermore, the silver halide grains may be the so-called conversion type, as described in British Pat. No. 635,841 and U.S. Pat. No. 3,622,318. Moreover, either silver halide grains of the kind which form latent images predominantly at the surface of the grains, or grains of the kind which mainly form latent images inside the grains can be used. These photographic emulsions are described in C. E. K. Mees, *The Theory of Photographic Process*, Macmillan, New York, P. Glafkides, *Chimie Photographique*, Paul Montel, Paris (1957), and so on, and therethrough, they are generally accepted. These photographic emulsions can be prepared using the methods described in, e.g., P. Glafkides, *Chimie et Physique Photographique*, Paul Montel, Paris (1967), G. F. Duffin, *Photographic Emulsion Chemistry*, The Focal Press, London (1966), V. L. Zelikman et al., *Making and Coating Photographic Emulsion*, The Focal Press, London (1964), and so on. Namely, any of processes, the acid process, the neutral process or the ammonia process, may be used for the preparation of the photographic emulsions. Suitable methods for reacting a water-soluble silver salt with a water-soluble halide include, e.g., a single jet method, a double jet method or a combination thereof.

A method in which silver halide grains are produced in the presence of excess silver ion (the so-called reversal mixing method) can also be employed in the present invention. On the other hand, the so-called controlled double jet method, in which the pAg of the liquid phase in which silver halide grains are to be precipitated is maintained constant, may be employed herein.

According to this method, a silver halide emulsion having a regular crystal form and almost uniform grain sizes can be obtained.

A mixture of two or more kinds of silver halide emulsions prepared separately may be employed.

In a process of producing silver halide grains or allowing the produced silver halide grains to ripen physically, cadmium salts, zinc salts, lead salts, thallium salts, iridium salts or complex salts thereof, rhodium salts or complex salts thereof, iron salts or complex salts thereof and/or so on may be present.

Removal of the soluble salts from the silver halide emulsion is, in general, carried out after the formation of the silver halide or after physical ripening. The removal can be effected using the noodle washing method which has been known from old and comprises gelling the gelatin, or using a sedimentation process (thereby causing flocculation in the emulsion) taking advantage of a sedimenting agent such as a polyvalent anion-containing inorganic salt (e.g., sodium sulfate), an anionic surface active agent, an anionic polymer (e.g., polystyrenesulfonic acid), or a gelatin derivative (e.g., an aliphatic acylated gelatin, an aromatic acylated gelatin, an aromatic carbamoylated gelatin or the like). The removal of soluble salts from the silver halide emulsion may be omitted.

The silver halide emulsion of the present invention can be a so-called un-after-ripened emulsion (e.g., a primitive emulsion), that is to say, a chemically unsensitized emulsion. However, it is usually chemically sensitized. Chemical sensitization can be carried out using processes described in P. Glafkides, supra, V. L. Zelikman et al., supra, or H. Frieser, Die Gründlagen der PHotographischen Prozesse mit Silberhalogeniden, Akademische Verlagsgesellschaft (1968).

The photographic emulsion layers and other hydrophilic colloidal layers which constitute the sensitive material of the present invention may contain various kinds of surface active agents as a coating aid and other wide variety of purposes, for example, preventing the generation of static charges, improvement in slipping facility, emulsifying dispersion, prevention from adhesion, improvement in photographic characteristics (e.g., acceleration of development, heightening of contrast, sensitization, etc.) and so on.

Examples of suitable surface active agents include nonionic ones such as saponin (steroid type), alkylene oxide derivatives (e.g., polyethylene glycol, polyethylene glycol/polypropylene glycol condensate, polyethylene glycol alkyl ethers or polyethylene glycol alkyl aryl ethers, polyethylene glycol esters, polyethylene glycol sorbitan esters, polyalkylene glycol alkylamines or amides, polyethylene oxide adducts of silicones, etc.), glycidol derivatives (e.g., alkenylsuccinic acid polyglycerides, alkylphenol polyglycerides, etc.), fatty acid esters of polyhydric alcohols, alkyl esters of sugar and so on; anionic ones which contain acid groups such as a carboxylic group, a sulfo group, a phospho group, a sulfate group, a phosphate group, etc., such as alkylcarboxylates, alkylsulfonates, alkylbenzenesulfonates, alkylnaphthalenesulfonates, alkylsulfuric acid esters, alkylphosphoric acid esters, N-acyl-N-alkyltaurines, sulfosuccinic acid esters, sulfoalkylpolyoxyethylene alkyl phenyl ethers, polyoxyethylene alkylphosphoric acid esters, etc.; amphoteric ones such as amino acids, aminoalkylsulfonic acids, aminoalkylsulfuric acid or aminoalkylphosphoric acid esters, alkylbetaines, amineoxides, etc.; and cationic ones such as alkylamine salts, aliphatic or aromatic quaternary ammonium salts, quaternary ammonium salts of heterocyclic rings like pyridinium, imidazolium, etc., phosphonium or sulfonium salts containing aliphatic or heterocyclic rings, and so on.

Magenta color images formed from the magenta coupler of the present invention come to have improved fastness to light if it is used in combination with a color image stabilizing agent represented by the following general formula (XV):

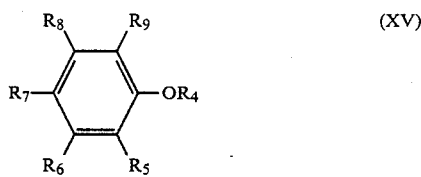

wherein $R_4$ represents a hydrogen atom, an alkyl group, an aryl group or a heterocyclyl group; $R_5$, $R_6$, $R_8$ and $R_9$ each represents a hydrogen atom, a hydroxy group, an alkyl group, an aryl group, an alkoxy group or an acylamino group; and $R_7$ represents an alkyl group, a hydroxy group, an aryl group or an alkoxy group. In the foregoing formula (XV), $R_4$ and $R_5$ may combine with each other and form a 5- or 6-membered ring, and in such a case, $R_7$ must be a hydroxy group or an alkoxy group. Further, $R_4$ and $R_5$ may combine with each other and form a methylenedioxy ring. Furthermore, $R_7$ and $R_8$ may combine with each other and form a 5-membered hydrocarbon ring, and in such a case, $R_4$ must be an alkyl group, an aryl group or a heterocyclyl group. In the substituents $R_4$ to $R_9$, an alkyl group and an alkyl moiety contain 1 to 22 carbon atoms, and an aryl group and an aryl moiety contain 6 to 22 carbon atoms.

Suitable addition amount of the color image stabilizing agent of the general formula (XV) is from 0.01 to 5.0 moles, preferably 0.05 to 1.0 mole, per mole of the magenta coupler of the formula (I) of the present invention.

These compounds may further include those described in U.S. Pat. Nos. 3,935,016, 3,982,944 and 4,254,216, published unexamined Japanese Patent Applications Nos. 21004/80 and 145530/79, British Patent Applications Nos. 2,077,455A and 2,062,888A, U.S. Pat. Nos. 3,764,337, 3,432,300, 3,574,627 and 3,573,050, published unexamined Japanese Patent Applications No. 152225/77, 20327/78, 17729/78 and 6321/80, British Pat. No. 1,347,556, British Patent Application No. 2,066,975A, published examined Japanese Patent Applications Nos. 12337/79 and 31625/73, and U.S. Pat. No. 3,700,455.

A preferred embodiment of the present invention consists in a silver halide color photographic material in which the coupler of the present invention is incorporated.

EXAMPLE 1

In separate 10 ml portions of ethanol, Coupler (1) and a comparative coupler represented by the chemical structural formula (A) illustrated hereinafter were dissolved in the same amount of 1.1 milli mole. In each of the resulting solutions, 1.3 milli mole of 4-N-ethyl-N-(2-methanesulfonamidoethyl)amino-2-methylaniline monosulfate, which acts as a color developing agent, was suspended. Thereto, a water solution of 12.9 milli mole of anhydrous sodium carbonate dissolved in 5 ml of water was added and stirred at room temperature. To the resultant mixed solution, 10 ml of a water solution containing 2.4 milli mole of potassium persulfate was slowly added dropwise.

After the stirring was continued for 1 hour at room temperature, the thus obtained reaction mixture was subjected to an extraction treatment using a mixture of 50 ml of ethyl acetate and 30 ml of water. The ethyl acetate layer was washed thoroughly with a saturated water solution of sodium chloride and then the solvent was removed therefrom. The residue was separated by silica gel chromatography using ethylether as the eluent. The NMR spectrum of the magenta dye produced from Coupler (1) of the present invention revealed, when measured in acetone-$d_6$ solvent, conspicuous absorption of two protons at $\delta=7.25$ ppm (1H, d, J=1.2 Hz) and $\delta=7.45$ ppm (1H, d, J=1.2 Hz) in addition to absorption band corresponding to protons of the color developer moiety in the aromatic proton range and thereby the structure of the magenta dye was confirmed to have the following chemical formula (B).

Comparative Coupler (A)

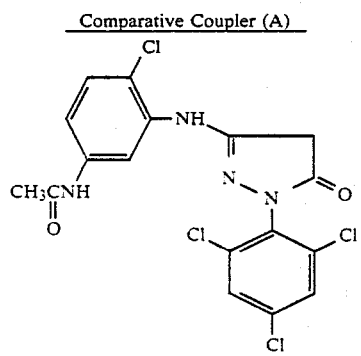

Magenta Dye (B)

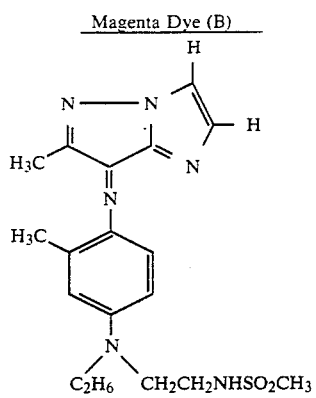

(wherein hydrogen atoms in circles correspond to the protons exhibiting the above-described chemical shifts in the NMR spectrum).

Visible abosrption spectra of Magenta Dye (B) and the magenta dye produced from Comparative Coupler (A), which were dissolved in ethyl acetate separately, are shown in FIG. 1. The absorptivity of each absorption spectrum was normalized taking the maximum intensity as 1.0 for facilitating the comparison.

As can be seen from FIG. 1, the coupler of the present invention has no side absorption in the vicinity of 400 to 430 nm, and the foot of its absorption band on the longer wavelength side was cut sharply. Therefore, the coupler of the present invention is of great advantage in reproducing color when used in a color photographic material.

Visible absorption spectra of Magenta Dye (C) and Magenta Dye (D) measured in ethyl acetate solvent, which dyes were produced from Coupler (8) and Coupler (9) of the present invention respectively using 4-N-ethyl-N-(2-methanesulfonamidoethyl)amino-2-methylaniline in the same manner as described above, are shown in FIG. 2. Therein, the absorptivity of each absorption spectrum was also normalized taking the maximum intensity as 1.0 for facilitating the comparison.

As can be seen from FIG. 2, in the couplers of the present invention, it has become feasible to shift the wavelength at which the absorption maximum reveals by changing the substituents. Further, the couplers of the present invention have no side absorptions in the vicinity of 400 to 430 nm and that the feet of their absorption bands on the longer wavelength side were cut sharply. Therefore, when used in a color photographic material, the couplers of the present invention are of great advantage in reproducing colors.

EXAMPLE 2

In a mixture of 15 ml of trioctyl phosphate and 15 ml of ethyl acetate, 13 g of a Comparative Coupler (E) illustrated below was dissolved. The resulting solution was added to 100 g of a 10% gelatin aqueous solution containing sodium di-sec-butylnaphthalenesulfonate, and stirred and emulsified by means of a homogenizing emulsifier to prepare an emulsion. This emulsion was mixed with 300 g portion of a green sensitive silver chlorobromide emulsion (containing 13.5 g of silver, and having a bromine content of 45 mol% and a chlorine content of 55 mol%) and thereto were added sodium dodecylbenzenesulfonate as a coating aid and 2-hydroxy-4,6-dichloro-s-triazine as a hardener. The thus prepared composition was coated on a cellulose triacetate support. Further, a gelatin coating solution was applied to the emulsion coat as a protective layer at a coverage of 1 g gelatin per square meter, and dried. The resultant film was named Film A.

Comparative Coupler (E)

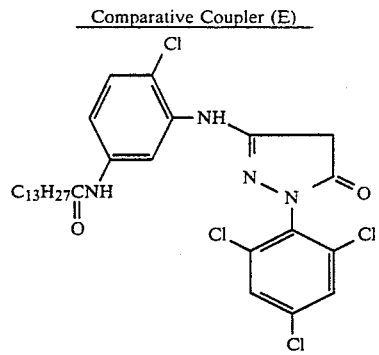

On the other hand, Film B and Film C were prepared using 5 g of Coupler (2) of the present invention and 8 g of Coupler (5) of the present invention respectively in the same manner as in the preparation of Film A.

Further, Film D was prepared in the same manner as in the preparation of Film A except that 8.2 g of Coupler (19) of the present invention was used and the green sensitive silver chlorobromide was used in an amount of 200 g.

Each of Films A to D was optically exposed by means of a sensitometer under the condition of 1,000 lux and 1 sec, and treated with the following processing solutions.

| Developing Solution | |
|---|---|
| Benzyl Alcohol | 15 ml |
| Diethylenetriaminepentaacetic Acid | 5 g |
| KBr | 0.4 g |
| $Na_2SO_3$ | 5 g |
| $Na_2CO_3$ | 30 g |
| Hydroxylamine Sulfate | 2 g |
| 4-Amino-3-methyl-N—ethyl-N—$\beta$-(methane-sulfonamido)ethylaniline . 3/2 $H_2SO_4.H_2O$ | 4.5 g |
| Water to make | 1,000 ml |
| pH adjusted to | 10.1 |
| Bleach-Fix Bath | |
| Ammonium Thiosulfate (70 wt %) | 150 ml |
| $Na_2SO_3$ | 5 g |
| Na[Fe(EDTA)] | 40 g |
| EDTA | 4 g |
| Water to make | 1,000 ml |
| pH adjusted to | 6.8 |

| Processing Step | Temperature (°C.) | Time |
|---|---|---|
| Development | 33 | 3 min 30 sec |
| Bleach-Fix | 33 | 1 min 30 sec |
| Washing | 28–35 | 3 min |

Densities of dye images obtained by having received the above-described processings were measured with a Macbeth densitometer through a status AA filter. Further, the visible absorption spectra of the dye images were measured with a spectrophotometer. Absorption of each dye image of the present invention on the film had no side absorption and its foot on the longer wavelength side was cut sharply in analogy with the result of Example 1. Color forming characteristics are given in the following Table 1.

TABLE 1

| Film | Coupler | Ag/Cp. by Mole | Maximum Density | Absorption Maximum (nm) | Intensity of Side Absorption (420 nm) |
| --- | --- | --- | --- | --- | --- |
| A | Comparative Coupler (E) | 6 | 2.62 | 535 | 0.137 |
| B | Coupler (2) | 6 | 2.71 | 530 | 0.041 |
| C | Coupler (5) | 6 | 2.60 | 526 | 0.052 |
| D | Coupler (19) | 4 | 3.10 | 526 | 0.053 |

Therein, intensities of side absorption are relative values obtained by taking the maximum intensity of their respective absorption spectra as 1.

The couplers of the present invention have turned out to provide sufficiently high coloration densities, compared with that of a conventional 5-pyrazolone type coupler. In particular, a 2-equivalent coupler represented by Coupler (19) has been found to provide a high coloration density, notwithstanding a small silver coverage.

In addition, intensities of the side absorption in the vicinity of 420 nm were lower with respect to the couplers of the present invention, compared with that of the comparative coupler. Therefore, excellent color reproduction can be achieved by the couplers of the present invention.

While the invention has been described in detail and with reference to specific embodiments thereof, it will be apparent to one skilled in the art that various changes and modifications can be made therein without departing from the spirit and scope thereof.

What is claimed is:

1. A method of forming a magenta color image, comprising the steps of:
   exposing a silver halide photosensitive material; and developing the material to form an image, using a developing solution containing an aromatic primary amine, the developing being carried out in the presence of a coupler represented by the following general formula (I):

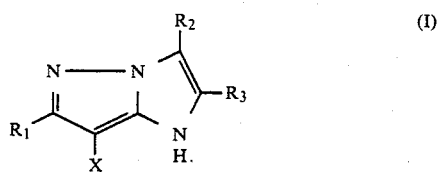

wherein $R_1$, $R_2$ and $R_3$ independently represent a hydrogen atom or a substituent group, and X represents a hydrogen atom or a coupling eliminable group.

2. A method of forming a magenta color image as claimed in claim 1, wherein $R_1$, $R_2$ and $R_3$ independently represent a hydrogen atom, an aliphatic residue, an aryl group, a heterocyclyl group, a cyano group, an alkoxy group, an aryloxy group, an acylamino group, an anilino group, a ureido group, a sulfamoylamino group, an alkylthio group, an arylthio group, an alkoxycarbonylamino group, a sulfonamido group, a carbamoyl group, a sulfamoyl group, a sulfonyl group, a heterocyclyloxy group, an acyloxy group, a carbamoyloxy group, a silyloxy group, an aryloxycarbonylamino group, an imido group, a heterocyclylthio group, a sulfinyl group, a phosphonyl group, an aryloxycarbonyl group, an acyl group, or an alkoxycarbonyl group.

3. A method of forming a magenta color image as claimed in claim 2, wherein X represents a hydrogen atom, a halogen atom, a carboxy group, or a coupling eliminable group which is attached to a pyrazole nucleus through an oxygen atom, a nitrogen atom, a sulfur atom or a carbon atom.

4. A method of forming a magenta color image as claimed in claim 1, wherein $R_2$ and $R_3$ combined with each other to form a 5-, 6- or 7-membered ring other than an aromatic ring.

5. A method of forming a magenta color image as claimed in claim 1, wherein the coupler of the general formula (I) is present in the photosensitive material.

6. A method of forming a magenta color image as claimed in claim 5, wherein the coupler of the general formula (I) is present in the material in an amount in the range of from $2 \times 10^{-3}$ mole to $5 \times 10^{-1}$ mole per 1 mole of silver halide.

7. A method of forming a magenta color image as claimed in claim 6, wherein the coupler of the general formula (I) is present in the material in an amount in the range of from $1 \times 10^{-2}$ mole to $5 \times 10^{-1}$ mole per 1 mole of silver halide.

8. A method of forming a magenta color image as claimed in claim 1, wherein the coupler of the general formula (I) is present in the developing solution.

9. A method of forming a magenta color image as claimed in claim 8, wherein the coupler of the general formula (I) is present in the developing solution in an amount in the range of 0.001 to 0.1 mole per 1,000 ml of the developing solution.

10. A method of forming a magenta color image as claimed in claim 9, wherein the coupler of the general formula (I) is present in the developing solution in an amount in the range of 0.01 to 0.05 mole per 1,000 ml of the developing solution.

11. A method of forming a magenta color image as claimed in claim 1, wherein the developing is carried out in the presence of a color image stabilizing agent represented by the following general formula (XV):

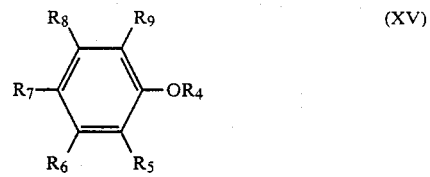

wherein $R_4$ represents a hydrogen atom, an alkyl group, an aryl group or a heterocyclyl group; $R_5$, $R_6$, $R_8$ and $R_9$ each represents a hydrogen atom, a hydroxy group, an alkyl group, an aryl group, an alkoxy group or an acylamino group; and $R_7$ represents an alkyl gorup, a hydroxy group, an aryl group or an alkoxy group.

12. A method of forming a magenta color image as claimed in claim 11, wherein the $R_4$ and $R_5$ of the color stabilizing agent combined with each other to form a 5- or 6-membered ring and further wherein $R_7$ is a hydroxy group or an alkoxy group.

13. A method of forming a magenta color image as claimed in claim 11, wherein the $R_4$ and $R_5$ of the color image stabilizing agent combined with each other to form a methylenedioxy ring.

14. A method of forming a magenta color image as claimed in claim 11, wherein the $R_7$ and $R_8$ of the color image stabilizing element combined with each other to form a 5-membered hydrocarbon ring and wherein the $R_4$ is an alkyl group, an aryl group or a heterocyclyl group.

15. A method of forming a magenta color image as claimed in claim 11, wherein an amount of the color image stabilizing agent of the general formula (XV) is from 0.01 to 5.0 moles per mole of the coupler of the general formula (I).

16. A method of forming a magenta color image as claimed in claim 15, wherein the amount of the color image stabilizing agent of the general formula (XV) is from 0.05 to 1.0 mole per mole of the coupler of the general formula (I).

* * * * *